United States Patent [19]
Dennill et al.

[11] Patent Number: 5,048,134
[45] Date of Patent: Sep. 17, 1991

[54] RESTRAINING DEVICE

[76] Inventors: Wayne R. Dennill; Richard E. Vollo, both of 935 Todd Road, Kamloops, Canada, V2C 5A9

[21] Appl. No.: 511,682

[22] Filed: Apr. 20, 1990

[30] Foreign Application Priority Data

Apr. 21, 1989 [CA] Canada .................................. 597479

[51] Int. Cl.⁵ ........................ A61G 1/00; A61G 1/044
[52] U.S. Cl. .................................. 5/82 R; 128/870
[58] Field of Search ............... 5/82 R, 82 B; 128/870, 128/871, 869

[56] References Cited

U.S. PATENT DOCUMENTS

| | | | |
|---|---|---|---|
| 2,899,692 | 8/1959 | Finken | 5/82 R |
| 3,889,668 | 6/1975 | Ochs et al. | 5/82 R |
| 4,127,120 | 11/1978 | Applegate | 5/82 R |
| 4,601,075 | 7/1986 | Smith | 5/82 R |
| 4,841,961 | 6/1989 | Burlage et al. | 5/82 R |
| 4,858,625 | 8/1989 | Cramer | 128/872 |

FOREIGN PATENT DOCUMENTS

| | | | |
|---|---|---|---|
| 723836 | 12/1965 | Canada | 5/27 |
| 748086 | 12/1966 | Canada | 2/41 |
| 809061 | 3/1969 | Canada | 227/17 |
| 48801 | 1/1988 | European Pat. Off. | 5/82 R |

*Primary Examiner*—Alexander Grosz
*Attorney, Agent, or Firm*—Trevor C. Klotz

[57] ABSTRACT

A novel restraining device for immobilizing a preselected portion of a prostrate human body when disposed on a body support platform or board having attachment locations has first and second panel sections which are detachably interconnectable in overlapping and variably adjustable relationship. Each panel section has extending therefrom adjustable attachment means, such as a pair of adjustable straps, which secure the panel section to the attachment locations. There may also be safety retaining means to ensure that the first and second panel sections are maintained in an interconnected relationship.

20 Claims, 4 Drawing Sheets

RESTRAINING DEVICE

FIELD OF THE INVENTION

The present invention relates to a novel restraining device for immobilizing a preselected portion of a human body when disposed on a body support platform having accompanying attachment locations.

The device is particularly suitable for use in immobilizing an injured person's body on site in an emergency situation, such as at the scene of an accident, where it may be necessary to quickly and easily immobilize part or all of the injured person's body so as to reduce the risk of further injury to the person.

BACKGROUND OF INVENTION

Various types of devices for restraining or immobilizing part or all of an injured person's body are known. One such device is the well known makeshift splint constructed of wire mesh or a length of rigid material, such as board. Where a person is more seriously injured, a device comprising a board onto which an injured person is secured using belting or bandages may be used.

These known devices as used in restraining an injured person's body suffer from a number of disadvantages. For example, it can take a considerable period of time to immobilize an injured person by tying or binding the person's body to a rigid support board using belts or bandages. As the process of immobilization with belts or bandages in conjunction with a rigid support board is time consuming, immobilization at the site of an accident may not be possible when it is imperative that the injured person be transported to a treatment location without delay. As well, the use of belts or bandages can result in pressure points on the injured person's body, restricted breathing, or increased discomfort to the injured person making padding necessary.

Furthermore, while some known immobilization devices or methods may, subsequent to immobilization, allow relatively ready access to one or more selected portions of the body (for example, where immediate medical attention is required) while continuing to immobilize the remainder of the body, re-immobilization of the accessed portion is difficult and time consuming, if not impossible.

It is thus desirable to have a device for securely restraining a preselected portion of an injured person's body, which may be easily and quickly utilized thus facillitating ready immobilization at the site of an accident. It is also desireable to have a restraining device which results in a reduced number of pressure points, which reduces the likelihood of restricted breathing, and which minimizes any discomfort to the injured person. Finally, it is desireable to have a restraining device which enables one to readily both access and subsequently re-immobilize one or more selected portions of an immobilized body.

SUMMARY OF THE INVENTION

The present invention relates to a restraining device for immobilizing a preselected portion of a prostrate human body when disposed on a body support platform having accompanying attachment locations. The device comprises first and second panel sections for placement over the preselected body portion, means on the first and second panel sections for detachably interconnecting the panel sections together in overlapping and variably adjustable relationship, and side attachment means extending from each of the first and second panel sections for securing the panel sections to selected attachment locations. The means for detachably interconnecting the panel sections together may comprise means frictionally engaging a surface of the first panel section to a surface of the second panel section.

In one embodiment of the invention, the first and second panel sections comprise a left panel section and a right panel section, and the side attachment means extending from the left panel section includes at least one adjustable strap extending outwardly from the left side of the left panel section, and the attachment means extending from the right panel section includes at least one adjustable strap extending outwardly from the right side thereof. In this embodiment of the invention, the means for detachably interconnecting the panel sections together comprises means frictionally engaging a surface of the left panel section to a surface of the right panel section.

In another embodiment of the invention, the first and second panel sections comprise an upper panel section and a lower panel section, and the attachment means includes at least one adjustable strap extending outwardly from each side (the non-overlapping sides) of each panel section. In this particular embodiment, the means for detachably interconnecting the panel sections together comprises means frictionally engaging a surface of the upper panel section to a surface of the lower panel section.

The preferred means for quickly detachably interconnecting the panel sections together is friction material such as a hook and loop type fastener, although at least one adjustable strap can be used for joining the two panel sections together in overlapping relationship.

The restraining device may be used in conjunction with any suitable body support platform such as a movable bed or a fracture board, having attachment locations thereon for the side attachment means..

In the case where a fracture board is employed, the attachment locations thereon can advantageously comprise a plurality of elongate apertures positioned along the longitudinal sides of the board and each aperture can include a slotted opening extending to the longitudinal edge of the board to facilitate entry of the straps into the slots.

If desired, where the means for detachably interconnecting the panel sections together comprises means frictionally engaging a surface of the first panel section to a surface of the second panel section, additional safety retaining means such as one or more adjustable safety straps can extend from the first panel section to the second panel section to maintain the first and second panel sections in an interconnected condition should the friction connection fail.

LIST OF DRAWINGS

In the accompanying drawings are illustrated several working embodiments of the invention:

DETAILED DESCRIPTION OF THE PREFERRED EMBODIMENTS

Figure 1:
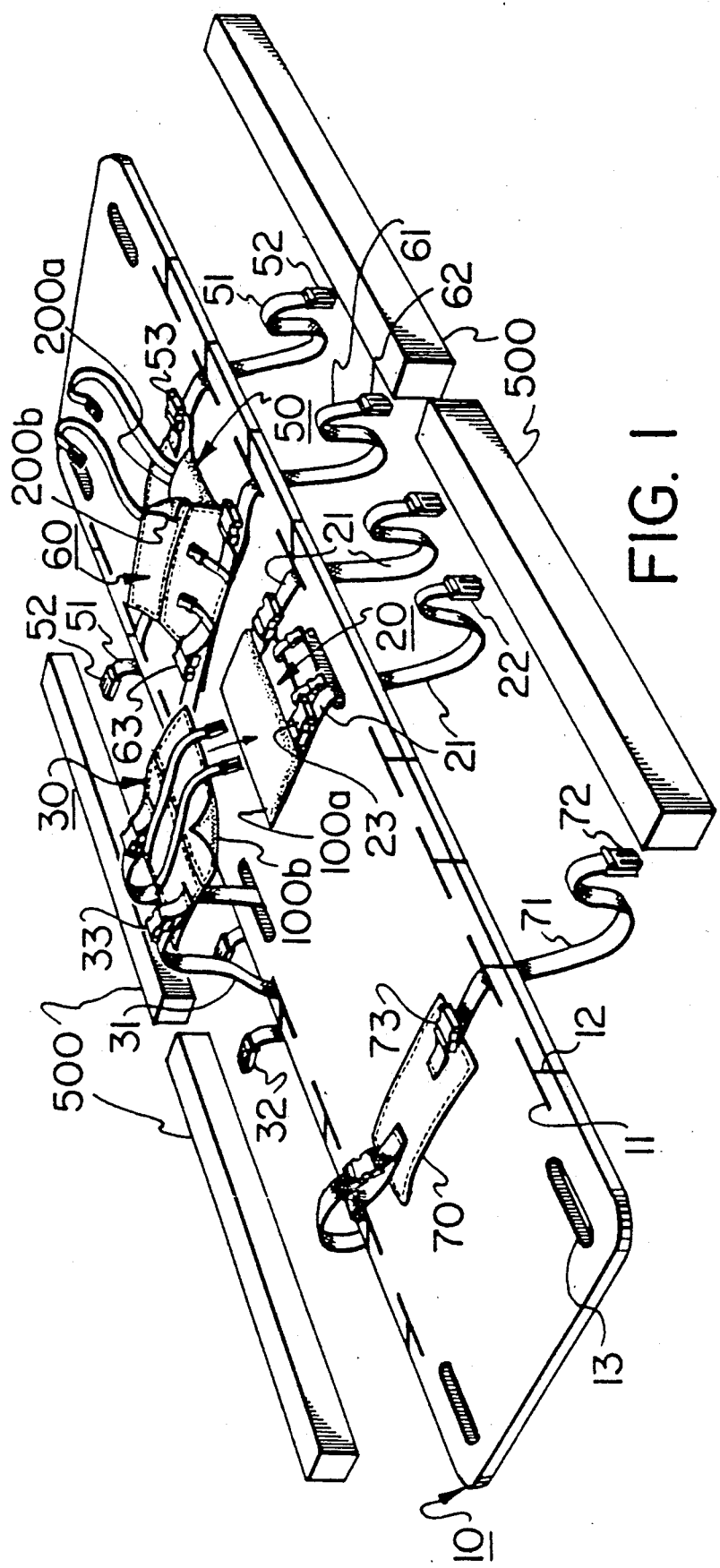
FIG. 1 is an exploded perspective view illustrating a fracture board and three different restraining devices.

In the description that follows, for convenience, like reference numerals are used on like parts illustrated in the drawings.

Referring to FIG. 1 of the drawings, there is illustrated a rigid body support platform in the form of a fracture board 10 which has a plurality of attachment locations illustrated as slots 11 aligned with one another along and parallel to each of adjacent longitudinal edges of board 10. Each slot 11 has an opening 12 extending from slot 11 to the adjacent longitudinal edge of board 10. Spaced inwardly from and along each longitudinal edge of board 10 are a plurality of handholds 13 aligned with one another and parallel to the adjacent edge of board 10, with one such handhold 13 located inward of and proximate to each of the opposite ends of each longitudinal edge of board 10 and another handhold 13 located midway therebetween as illustrated.

Figure 3:
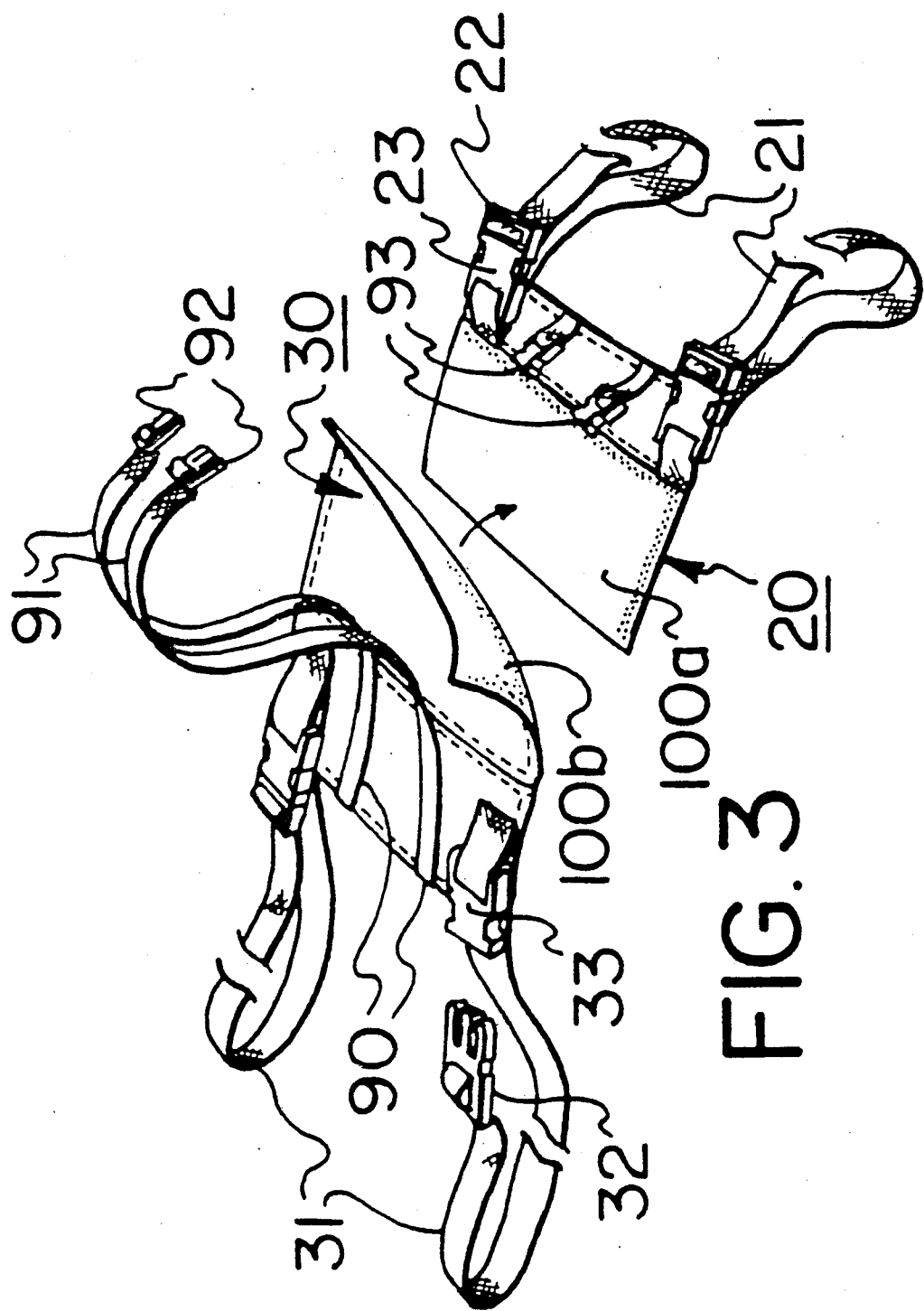
FIG. 3 is a perspective view of left and right hand panel sections and their associated attachment means.

Also illustrated in FIG. 1, and in greater detail in FIG. 3, is a first or left panel section 20 and a second or right panel section 30 of a first embodiment of the invention. The means of left panel section 20 and right panel section 30 for detachably interconnecting the two panel sections in overlapping and variably adjustable relationship is illustrated in FIGS. 1 and 3 as comprising mating areas 100a and 100b of a hook and loop type fastener on part of the upper surface of left panel section 20 and part of the lower surface of right panel section 30 respectively.

Extending inwardly from one side of left panel section 20 are a pair of adjustable straps 21, each having at its end remote from panel section 20 a flange 22 adapted to be releaseably engaged in a corresponding clasp 23 located on the upper surface of left panel section 20. As illustrated in FIGS. 1 and 3, similarly extending from right panel section 30 are a pair of adjustable straps 31, each having a flange 32 adapted for releaseable engagement in a clasp 33.

Figure 4:
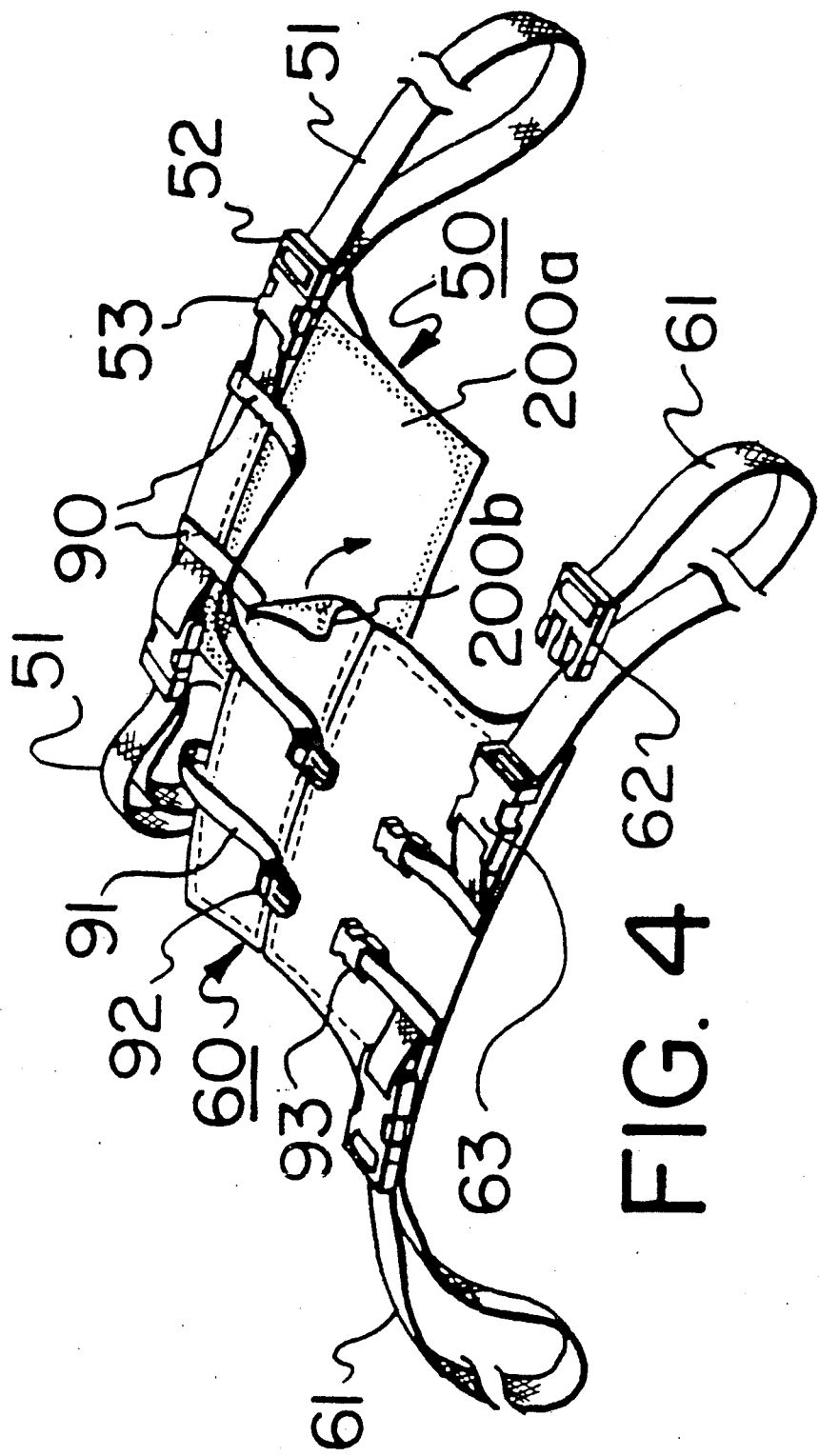
FIG. 4 is a perspective view of upper and lower panel sections and their associated attachment means.

Also illustrated in FIG. 1, and in greater detail in FIG. 4, is another embodiment of the invention comprised of lower panel section 50 and upper panel section 60, and respective associated attachment means. In this embodiment of the invention, each of a pair of adjustable straps 51 extends outwardly from opposite sides of lower panel section 50, and each of adjustable straps 61 similarly extend outwardly from upper panel section 60. As illustrated, each adjustable strap 51 (61) has at its end remote from the panel section a flange 52 (62) adapted for releasable engagement in clasp 53 (63). This means for detachably interconnecting upper and lower panel sections is illustrated in FIG. 4 as comprising mating areas 200a and 200b of a hook and loop type fastener located on adjacent surfaces of panel sections 50 and 60.

Figure 2:
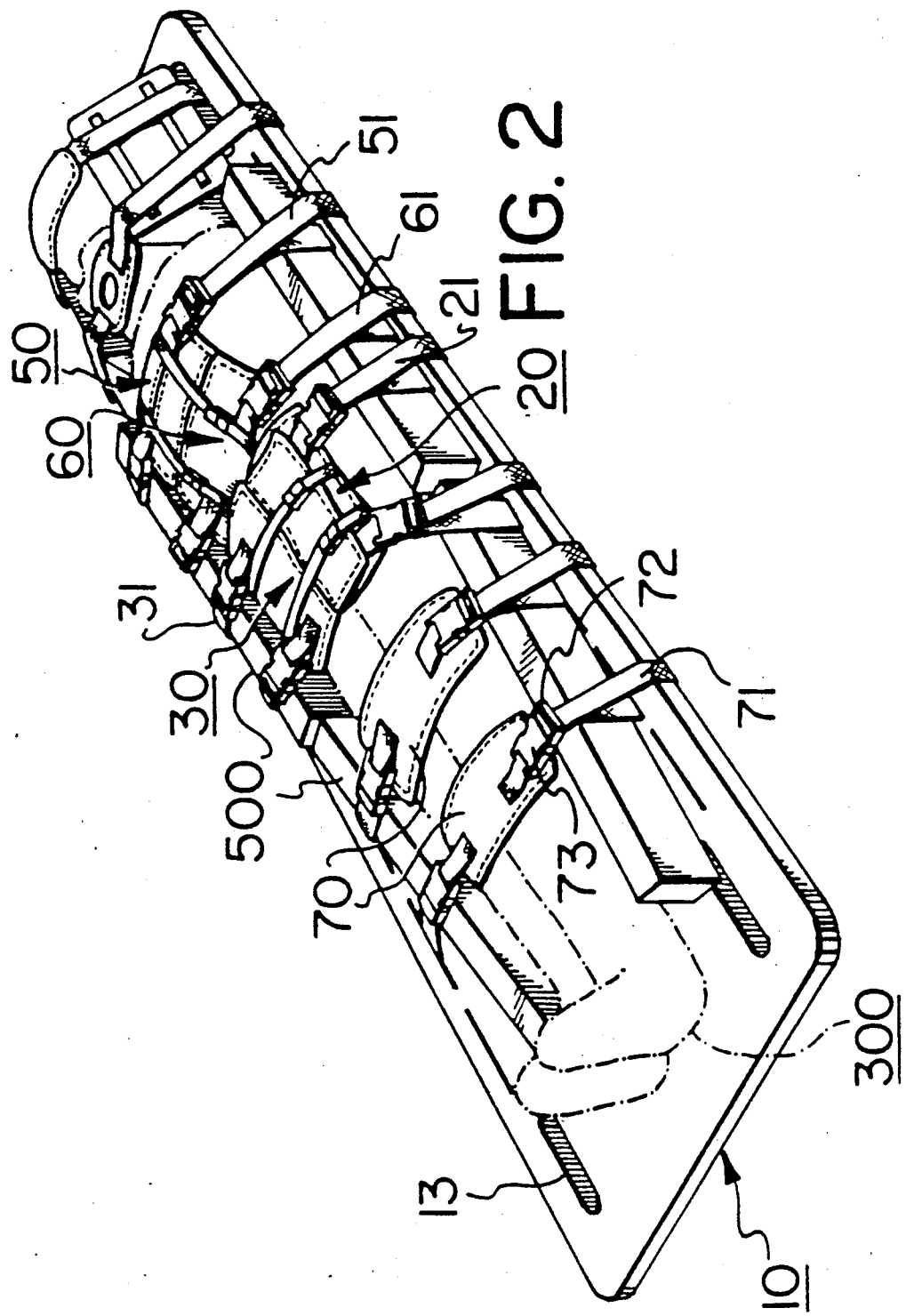
FIG. 2 is a perspective view of a totally immobilized in situ body on a fracture board employing in addition to the restraining device illustrated in FIG. 1 additional known restraining devices on the lower extremities and head of the body.

Illustrated in FIG. 2 of the drawings is an in situ body 300 totally immobilized on a fracture board 10 by the two previously described embodiments of the invention and additional known restraining devices.

As illustrated therein, the aforementioned embodiments of the invention are used to immobilize the chest and hip areas of the body whereas the knee, shin and head areas of the body are each immobilized by known devices. The device used to immobilize the knee and shin areas is illustrated in further detail in FIG. 1, and is comprised of a padded elongate band 70 having extending from each side thereof an adjustable strap 71 with a flange 72 adapted for releaseable engagement in a clasp 73 located on the upper surface of band 70.

In FIG. 3 of the drawings there is illustrated left and right hand sections 20 and 30 and their associated attachment means. Also illustrated are safety retaining means comprising a pair of adjustable belts 91 extending from anchor locations 90 on right panel section 30. Each belt 91 includes at its end remote from right panel section 30 a flange 92 adapted for releasable engagement in clasp 93 located on left panel section 20. The restraining device comprising upper and lower panel sections may include similar safety retaining means.

With reference to the drawings the use and operation the invention may be described as follows:

Prior to placement of the body of an injured person on board 10, each of straps 21 and 31 of the left and right panel sections is inserted into an appropriately located slot 11 by drawing the strap into and through associated opening 12. As well, one of each pair of adjustable straps 51 and 61 of lower and upper panel sections 50 and 60 is similarly placed in an appropriately located slot.

After the injured person's body has been placed and positioned on board 10, each left panel section 20 is placed atop the body and each adjacent right panel section 30 is brought over and onto left panel section 20 with the application of sufficient pressure to ensure adequate attachment of the mating areas of the hook and loop type fastener located on adjacent surfaces of the left and right panel sections.

Where the device comprised of upper and lower panel sections is used, after the body has been placed and positioned on board 10 each upper and lower panel section is drawn over top of the body, and the remaining free adjustable strap extending from each panel section is placed into an appropriately located slot 11 in the manner previously described. Thereafter, the adjacent hook and loop type fastener covered surfaces of adjacent upper and lower panel sections may be brought together as aforesaid to interconnect the upper and lower panel sections.

To ensure that the interconnecting panel sections of each device are maintained in an interconnected condition, each flange 92 located at the end of each adjustable strap 91 extending from one panel section is engaged in its corresponding clasp 93 located on the other interconnected panel section, and strap 91 adjusted to remove any slack in strap 91.

To secure the injured person's body onto the platform, each of flanges 22, 32, 52 and 62, with their attached adjustable straps, may be drawn outwardly and upwardly away from board 10 so that the panel sections are drawn downwardly onto the body toward board 10. Once the desired snugness of fit of panel sections on the body has been attained, each of the flanges may be engaged in its corresponding clasp, and the adjustable straps tightened or loosened to attain the desired fit for transport of the immobilized body.

Where it is desired to reduce even further the possibility of movement of the body during transport on the platform, illustrated in FIGS. 1 and 2, prior to drawing the panel sections over the body to be immobilized, one or more elongate pads 500 each of suitable dimensions may be placed along each side of the body to be immobilized. It will be appreciated that the dimensions of elongate pad 500 should be such that they function as packing elements between the body and the adjustable straps with a consequent reduction in the likelihood of movement of the body once immobilized on the platform.

Following immobilization of the body on the platform as aforesaid, two or more persons may grasp appropriate ones of handholds 13 and lift the platform and immobilized body for transport to a treatment location.

It will be appreciated that the present invention is not limited to the features of the embodiments so described and illustrated, but includes all variation and modifications within the scope of the claims.

We claim:

1. A restraining device for immobilizing a preselected portion of a prostrate human body (300) when disposed on a body support platform (10) having accompanying attachment locations (11), said device comprising first (20,50) and second (30,60) panel sections for placement over said body portion, quick coupling and release means (100a, 100b, 200a, 200b) on said first and second panel sections for detachably interconnecting said panel sections together in overlapping and variably adjustable relationship, and side attachment means (21, 22,31,32,51,52,61,62) extending from each of said first and second panel sections for securing said panel sections to said attachment locations, said first (20,50) and second (30,60) panel sections each including at least one adjustable variable length strap extending outwardly therefrom providing said side attachment means and wherein said panel sections (20,30) overlap one another in a direction across said body.

2. The restraining device as claimed in claim 1, wherein said means for detachably interconnecting said panel sections together comprises means frictionally engaging a surface (100a) of said first panel section (20) to a surface (100b) of said second panel section (30).

3. The restraining device as claimed in claim 2, wherein said device includes safety retaining means (91,92) extending from said first panel section (20) to said second panel section (30) to maintain said first and second panel sections in an interconnected condition.

4. The restraining device as claimed in claim 3, wherein said safety retaining means (91,92) comprises at least one adjustable strap.

5. The restraining device as claimed in claim 1, wherein said means for detachably interconnecting said panel sections together comprises at least one adjustable strap.

6. The restraining device as claimed in claim 1, in further combination with a body support platform (10), said platform comprising a fracture board, and wherein said attachment locations (11) are on said fracture board.

7. The restraining device as claimed in claim 1, in further combination with a body support platform (10), said platform comprising a fracture board, and wherein said attachment locations (11) comprise a plurality of elongate apertures positioned along the longitudinal sides of said board and each aperture includes a slotted opening (12) extending to the longitudinal edge of said board.

8. A restraining device for immobilizing a preselected portion of a prostrate human body (300) when disposed on a body support platform (10) having accompanying attachment locations (11), said device comprising first (20,50) and second (30,60) panel sections for placement over said body portion, quick coupling and release means (100a, 100b, 200a, 200b) on said first and second panel sections for detachably interconnecting said panel sections together in overlapping and variably adjustable relationship, and side attachment means (21, 22,31,32,51,52,61,62) extending from each of said first and second panel sections for securing said panel sections to said attachment locations, said side attachment means (21,22,31,32,51,52,61,62) including at least one adjustable variable length strap extending outwardly from each side edge of each panel section and wherein said panel sections (50,60) overlap in a direction lengthwise of said body.

9. The restraining device as claimed in claim 8, wherein said means for detachably interconnecting said panel sections together comprises means frictionally engaging a surface (200a) of said first panel section to a surface (200b) of said second panel section (60).

10. The restraining device as claimed in claim 9, wherein said device includes safety retaining means (91,92) extending from said first panel section (50) to said second panel section (60) to maintain said first and second panel sections in an interconnected condition.

11. The restraining device as claimed in claim 10, wherein said safety retaining means (91,92) comprises at least one adjustable strap.

12. The restraining device as claimed in claim 8, wherein said means for detachably interconnecting said panel sections together comprises at least one adjustable strap.

13. The restraining device as claimed in claim 8, in further combination with a body support platform (10), said platform comprising a fracture board, and wherein said attachment locations (11) are on said fracture board.

14. The restraining device as claimed in claim 8, in further combination with a body support platform (10), said platform comprising a fracture board, and wherein said attachment locations (11) comprise a plurality of elongate apertures positioned along the longitudinal sides of said board and each aperture includes a slotted opening (12) extending to the longitudinal edge of said board.

15. A restraining device for immobilizing a preselected portion of a prostrate human body (300) when disposed on a body support platform (10) having accompanying attachment locations (11), said device comprising first (20,50) and second (30,60) panel sections for placement over said body portion, quick coupling and release means (100a, 100b, 200a, 200b) on said first and second panel sections for detachably interconnecting said panel sections together in overlapping and variably adjustable relationship, and side attachment means (21, 22,31,32,51,52,61,62) extending from each of said first and second panel sections for securing said panel sections to said attachment locations, in further combination with a body support platform (10), said platform comprising a fracture board, and wherein said attachment locations (11) comprise a plurality of elongate apertures positioned along the longitudinal sides of said board and each aperture includes a slotted opening (12) extending to the longitudinal edge of said board.

16. A restraining device for immobilizing a preselected portion of a human body (300) when disposed on a body support platform (10) having accompanying attachment locations (11), said device comprising first (20,50) and second (30,60) panel sections for placement over said body portion, quick coupling and release means (100a,100b,200a,200b) on said first and second panel sections for detachably interconnecting said panel sections together in overlapping and variably adjustable relationship over said body portion, and side attachment means (21,22,31,32,51,52,61,62) including at least one adjustable variable length strap (21,31,51,61) extending outwardly from opposite edges of the panel sections when interconnected and wherein said interconnected panel sections and straps associated therewith extend over the body with said straps being anchored to said platform at said attachment locations.

17. The restraining device as claimed in claim 16, wherein said device includes safety retaining means extending from said first (20,50) panel section to said second (30,60) panel section to maintain said first and second panel sections in an interconnected condition.

18. The restraining device as claimed in claim 17, in further combination with a body support platform (10), said platform comprising a fracture board, and wherein said attachment locations (11) are on said fracture board.

19. A restraining device in combination with a body support platform (10) for restraining a preselected portion of a human body (300) disposed on said platform, said device comprising first (20,50) and second (30,60) panel sections for placement over said body portion, quick coupling and release means (100a,100b, 200a,200b) for detachably interconnecting said panel sections together in overlapping and variably adjustable relationship over said body portion, and at least one strap (21,31,51,61) extending outwardly from each of opposite edges of the panel sections when interconnected for anchoring said panel sections to said platform, said platform comprising a longitudinal board having a plurality of apertures (11) spaced inwardly from and along the longitudinal edges of said board, said apertures including a slotted opening (12) extending thereinto from the adjacent longitudinal edge of said board for insertion of the strap into said aperture, said interconnected panel sections and straps extending across the platform over said body portion disposed thereon.

20. The combination claimed in claim 19, wherein said device includes safety retaining means extending from said first (20,50) panel section to said second (30,60) panel section to maintain said panel sections in an interconnected condition.

* * * * *